United States Patent [19]
Rueter

[11] Patent Number: 5,944,745
[45] Date of Patent: Aug. 31, 1999

[54] IMPLANTABLE MEDICAL DEVICE CAPABLE OF PRIORITIZING DIAGNOSTIC DATA AND ALLOCATING MEMORY FOR SAME

[75] Inventor: John Carl Rueter, Shoreview, Minn.

[73] Assignee: Medtronic, Inc., Minneapolis, Minn.

[21] Appl. No.: 08/719,218

[22] Filed: Sep. 25, 1996

[51] Int. Cl.[6] .................. A61N 1/362; A61B 5/0452; A61B 5/0432

[52] U.S. Cl. .................................. 607/27; 600/515

[58] Field of Search .................. 607/9, 27, 28; 128/702; 600/515–518

[56] References Cited

U.S. PATENT DOCUMENTS

| | | |
|---|---|---|
| 4,374,382 | 2/1983 | Markowitz . |
| 4,476,868 | 10/1984 | Thompson . |
| 4,556,063 | 12/1985 | Thompson et al. . |
| 4,566,030 | 1/1986 | Nickerson et al. . |
| 4,583,553 | 4/1986 | Shah et al. ............................... 128/704 |
| 4,675,842 | 6/1987 | Szenes et al. . |
| 5,007,431 | 4/1991 | Donehoo, III .......................... 128/696 |
| 5,052,388 | 10/1991 | Sivula et al. . |
| 5,127,404 | 7/1992 | Wyborny et al. . |
| 5,217,021 | 6/1993 | Steinhaus et al. ...................... 128/702 |
| 5,261,401 | 11/1993 | Baker et al. ................................. 607/9 |
| 5,285,792 | 2/1994 | Sjoquist et al. ........................... 607/27 |
| 5,312,446 | 5/1994 | Holschbach et al. ....................... 607/9 |
| 5,345,362 | 9/1994 | Winkler . |
| 5,513,645 | 5/1996 | Jacobson et al. ......................... 607/27 |
| 5,518,001 | 5/1996 | Snell . |

*Primary Examiner*—William E. Kamm
*Assistant Examiner*—Carl H. Layno
*Attorney, Agent, or Firm*—Thomas F. Woods; Harold R. Patton

[57] ABSTRACT

A body implantable device having at least one physiologic sensor capable of monitoring performance of the device and physiologic indicators of the patient is disclosed. The device is capable of determining whether an event or indicator being monitored is beyond certain threshold levels that indicate an event or indicator may be clinically significant. The device can determine the relative importance of the event or indicator in contrast to other events or indicators for which data have been previously stored. The device is further capable of allocating memory for data relating to the higher priority events or indicators.

4 Claims, 5 Drawing Sheets

IMPLANTABLE MEDICAL DEVICE CAPABLE OF PRIORITIZING DIAGNOSTIC DATA AND ALLOCATING MEMORY FOR SAME

FIELD OF THE INVENTION

This invention relates to the field of body-implantable devices, and more particularly relates to a method and apparatus for performing diagnostics on the system including the implantable device as well as on physiological conditions, and managing memory within the device so as to store the maximum amount of the most important and comprehensive data for retrieval from the device.

BACKGROUND OF THE INVENTION

Various types of automatic, body-implantable medical devices such as cardiac pacemakers, cardiac defibrillators, cardioverters, neural stimulators and the like, have been shown in the prior art. The majority of these products offer a full range of diagnostic routines that can be selected by the physician or medical technician. As the diagnostic capabilities of the devices increase the selection process by the physician or technician becomes that much more complicated. Upon implantation, or at any other point when the device is being accessed, the doctor must try to look into the future to determine what may happen so that he or she may determine what diagnostic routines to select. The underlying problem is that devices today have far more ability to capture diagnostic data than they have the memory capacity to store.

Because of the lack of memory, physicians and technicians are forced to select which parameters to track. If the physician has chosen to track the frequency and extent of ventricular tachycardia, then atrial undersensing due to a lead that is rapidly failing may not be detected. What is needed is an implantable device that is capable of selecting at any given time what is most important to track. The device should further be capable of allocating the limited memory available within the device for storage of the most important data collected since the last interface with the device.

SUMMARY OF THE INVENTION

In view of the foregoing considerations, the present invention is directed to an implantable medical device that is capable of performing continuous diagnostics, and selecting from those diagnostics the more critical information to store in memory specifically allocated by the device. The implantable device generally could contain a CPU for controlling all aspects of the device's diagnostic operation, a read only memory ("ROM") for storing the various diagnostic or monitoring routines, and random access memory ("RAM") for storing collected data.

Monitoring or diagnostic routines for tracking a variety of system operations are stored in ROM. Examples of system operations that can be monitored are: lead impedance, atrial or ventricular under or over sensing, episodes of atrial tachycardia, onset and cessation of 2:1 block, and changes in p- or r-wave length or amplitude. This list of examples by no means encompasses all possible diagnostics which may be performed on or by a pacemaker, but is given merely to serve as an indication of the types of data that can be monitored.

The CPU is capable of performing all diagnostic routines. In the present invention the CPU performs all monitoring and data collection and from that collected data determines which data takes on clinical significance. Once the CPU determines that an event is clinically significant, the CPU will allocate memory in the RAM for storage of data with respect to that event. If the available memory is full the CPU determines whether the new event is either more important than a previously stored event. If so, then the previously stored event is overwritten by data from the new event or the old, new, or both old and new data are compressed so that both can be stored.

Under the present invention the physician or clinician at the next interface with the implantable device using a body external programmer will receive data on clinically significant events that have occurred since the last interface. This is an improvement over receiving only the data requested from the last interface, because the problems of possibly not capturing the more important events occurring with the patient or the device has been overcome.

The present invention offers tremendous flexibility. The physician for instance may want to set a default that collects data on certain events unless the CPU determines that a more clinically significant event has occurred. The selection of the importance or clinical significance of given events may be standardized across a product line or may be customized for a particular model, physician, or patient.

BRIEF DESCRIPTION OF THE DRAWINGS

The foregoing and other aspects of the present invention are best appreciated with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
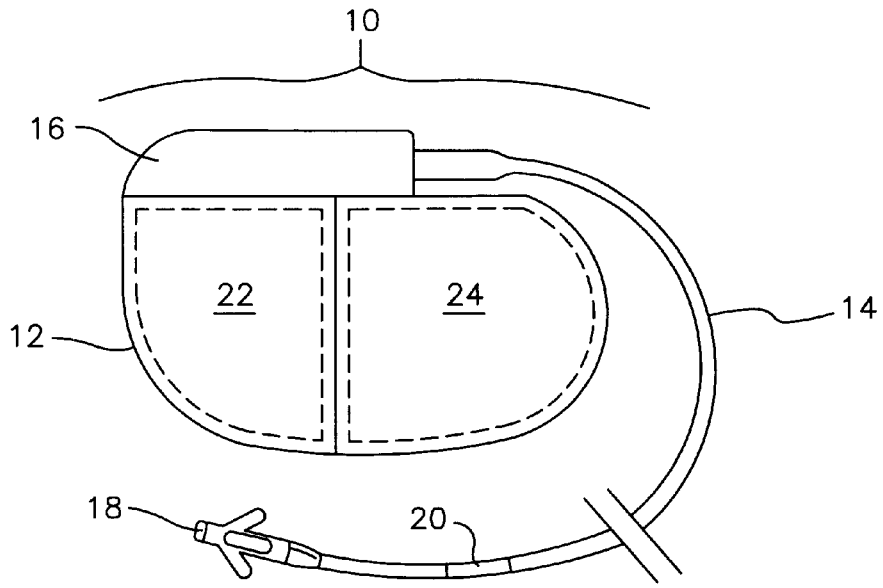
FIG. 1 is a cross-section of an implantable pacemaker and lead.

Referring to FIG. 1, there is illustrated a body-implantable pacemaker system 10 in accordance with a presently preferred embodiment of the invention. As shown in FIG. 1, pacemaker system 10 includes a pulse generator housed within a hermetic enclosure 12, and a flexible, elongate lead 14 coupled to a header or connector block assembly 16 associated with pulse generator enclosure 12. In the presently preferred embodiment, enclosure 12 is made of titanium or another suitable biocompatible material, and header 16 is made of polyurethane or the like. In accordance with conventional practice, lead 14 comprises one or more electrical conductors insulated with a flexible outer sheath made of silicone rubber, polyurethane, or the like. Lead 14 has one or more electrodes disposed generally at the distal end thereof, lead 14 in FIG. 1 being shown as a bipolar lead having a tip electrode 18 and a ring electrode 20, further in accordance with conventional practice.

Header 16 encases one or more hermetic feedthrough elements (not shown in the Figures) for enabling electrical signals to be communicated between the conductors of lead 14 and electronic stimulation and control circuitry 22 disposed within hermetic enclosure 12. Also disposed within hermetic enclosure 12 is a battery 24 for providing power to the various electronic components of pacemaker system 10.

Figure 2:
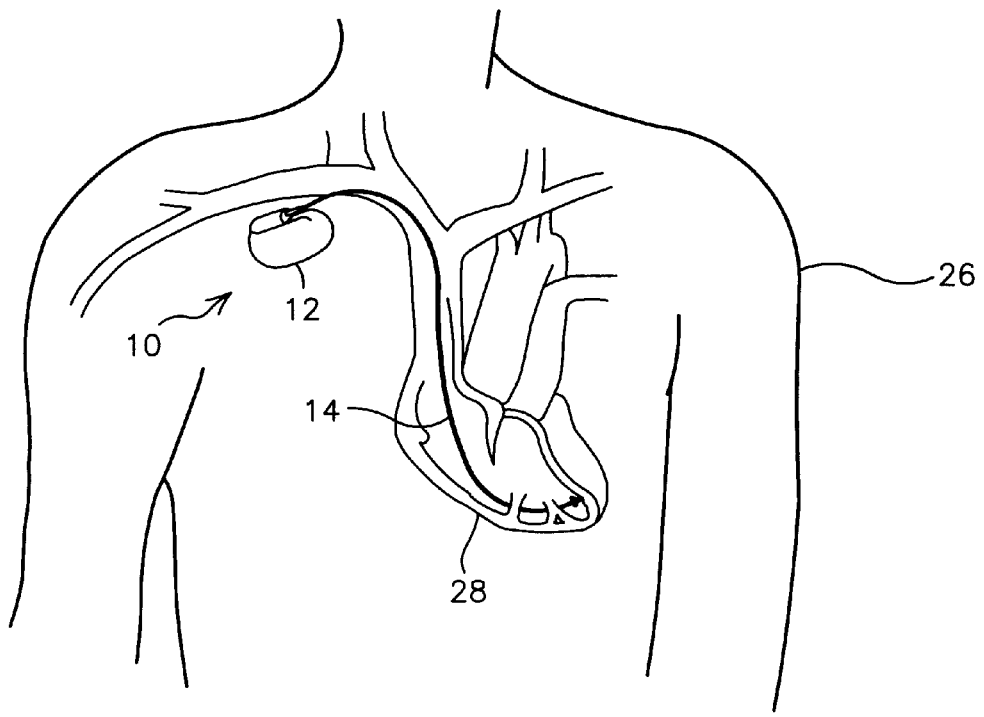
FIG. 2 is a cross-section of a patient with the device and lead of FIG. 1 implanted.

FIG. 2 shows a conventional lateral transvenous implantation of pacemaker system 10 within the body of a patient 26. Hermetic enclosure 12 is disposed within a small subcutaneous pocket inferior to the patient's clavicle. Lead 14 extends transvenously from enclosure 12 such that its distal end is disposed within the heart 28 of patient 26.

Figure 3:
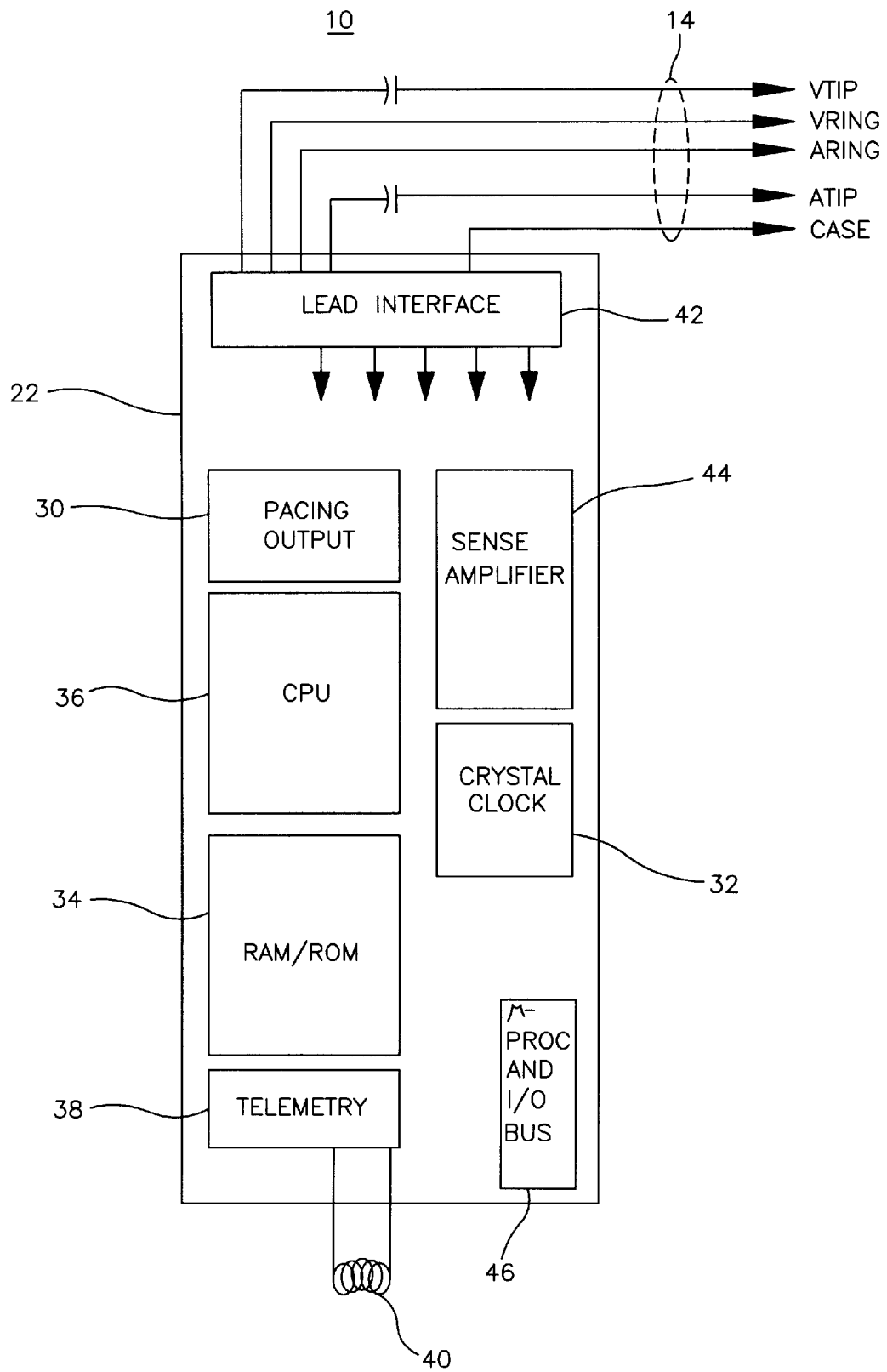
FIG. 3 is a functional block diagram of a preferred embodiment of an implantable device.

Turning now to FIG. 3, there is shown a functional block diagram of pacemaker system 10 and in particular, the organization of electronic stimulation and control circuitry 22 in accordance with the presently disclosed embodiment of the invention. In accordance with conventional practice, stimulation and control circuitry 22 functions to control the device's pacing and sensing functions. Stimulation and control circuit 22 may be of conventional design, in accordance, for example, with what is disclosed U.S. Pat. No. 5,052,388 to Sivula et al., entitled "Method and Apparatus for Implementing Activity Sensing in a Pulse Generator", which patent is hereby incorporated by reference herein in its entirety. To the extent that certain components of pacemaker system 10 are conventional in their design and operation, such components will not be described herein in extensive detail, as it is believed that design and implementation of such components would be a matter of routine to those of ordinary skill in the art. For example, stimulation and control circuit 22 in FIG. 3 includes stimulating pulse output circuitry 30, a crystal oscillator 32, a random-access memory and read-only memory (RAM/ROM) unit 34, and a central processing unit (CPU) 36, all of which are well-known in the art.

Pacemaker 10 also includes an internal communication/telemetry circuit 38 so that it is capable communicating with an external programmer/control unit not shown in the Figures. An example of such an external programmer is disclosed in U.S. Pat. No. 5,345,362 to Winkler, which is hereby incorporated by reference in its entirety. Associated with communication circuit 38 is a radio-frequency antenna 40 for facilitating the receipt and transmission of radio-frequency signals, in accordance with conventional practice and as exemplified by the teachings of U.S. Pat. No. 4,374,382 to Markowitz, entitled "Marker Channel Telemetry System for a Medical Device," of U.S. Pat. No. 5,127,404 to Wyborny et al., entitled "Telemetry Format for Implanted Medical Device," and of U.S. Pat. No. 4,556,063 to Thompson et al., entitled "Telemetry System for a Medical Device." The Markowitz '382, Wyborny et al. '404 and Thompson et al. '063 patents are each hereby incorporated by reference herein in their respective entireties.

In one embodiment of the invention, CPU 36 is a custom microprocessor adapted to fetch and execute instructions stored in RAM/ROM unit 34 in a conventional manner. It is contemplated, however, that other implementations may be suitable for the purposes of practicing the present invention. For example, an off-the-shelf, commercially available microprocessor or microcontroller, or custom application-specific, hardwired logic, or state-machine type circuitry may be utilized to perform the stimulation and control functions of CPU 36. Furthermore, while the present invention is described herein in the context of an automatic, body-implantable pacemaker system, it is contemplated that the present invention may find beneficial applicability in connection with automatic medical device systems other than pacemakers, including, for example, defibrillators, tachycardiac conversion devices, and the like, whether body-implantable or external.

With continued reference to FIG. 3, stimulation and control circuitry 22 is coupled to one or more leads 14 which, when implanted, extend transvenously between the implant site of pulse generator 10 and the patient's heart 28, as previously noted with reference to FIG. 2. Physically, the connections between leads 14 and the various internal components of circuitry 22 are facilitated by means of a conventional connector block assembly 16, shown in FIG. 2 but not shown in FIG. 3. Electrically, the coupling of the conductors of leads and internal electrical circuitry 22 is facilitated by means of a lead interface circuit 42 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, which serve as physiologic sensors, as would be familiar to those of ordinary skill in the art. For the sake of clarity, the specific connections between the conductors of lead 14 and the various components of stimulation and control circuitry 22 are not shown in FIG. 3, although it will be clear to those of ordinary skill in the art that, for example, conductors in lead 14 will necessarily be coupled, either directly or indirectly, to sense amplifier circuitry 44 and stimulating pulse output circuit 30, in accordance with common practice, such that cardiac electrical signals may be conveyed to sensing circuitry 44, and such that stimulating pulses may be delivered to cardiac tissue, via lead 14.

As previously noted, stimulation control circuit 22 includes central processing unit 36 which may be an off-the-shelf programmable microprocessor or microcontroller, but in the presently preferred embodiment of the invention is a custom integrated circuit. Although specific connections between CPU 36 and other components of stimulation and control circuit 22 are not shown in FIG. 3, it will be apparent to those of ordinary skill in the art that CPU 36 functions to control the timed operation of stimulating pulse output circuit 26 and sense amplifier circuit 44 under control of programminig stored in RAM/ROM unit 34. It is believed that those of ordinary skill in the art will be familiar with such an operative arrangement.

With continued reference to FIG. 3, crystal oscillator circuit 32, in the presently preferred embodiment a 32,768-Hz crystal controlled oscillator, provides main timing clock signals to stimulation and control circuit 22. Again, the lines over which such clocking signals are provided to the various timed components of stimulation and control circuitry 22 (e.g., microprocessor 36) are omitted from FIG. 3 for the sake of clarity.

Various other interconnections between individual components of stimulation and control circuit 22 are represented by microprocessor and I/O Bus block 46 in FIG. 3. For example, there is preferably a connection between CPU 36 and pacing output circuit 30, such that CPU 36 can provide triggering or inhibiting signals to output circuit 30 to control the delivery of stimulating pulses to the patient's heart 28. These various interconnections are also omitted from FIG. 3 for the sake of clarity.

It is to be understood that the various components of pacemaker system 10 depicted in FIG. 3 are powered by means of battery 24 (not shown in FIG. 3) which is contained within the hermetic enclosure of pacemaker 10 as depicted in FIG. 1. For the sake of clarity in the Figures, the battery and the connections between it and the other components of pulse generator 10 are not shown other than in FIG. 1.

Stimulating pulse output circuit 30, which functions to generate cardiac stimuli under control of signals issued by CPU 36, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

Sense amplifier circuit 44, which will be hereinafter described in further detail, functions to receive electrical cardiac signals over lead 14 and to process such signals to derive event signals reflecting the occurrence of specific cardiac electrical events, including atrial contractions (P-waves) and ventricular contractions (R-waves). These event-indicating signals are provided to CPU 36 for use in controlling the synchronous stimulating operations of pulse generator 10 in accordance with common practice in the art. In addition, these event indicating signals may be communicated, via uplink transmission, to an external programming unit for visual display to a physician or clinician.

Those of ordinary skill in the art will appreciate that pacemaker system 10 may include numerous other components and subsystems, for example, activity sensors and associated circuitry. The presence or absence of such additional components in pacemaker 10, however, is not believed to be pertinent to the present invention, which relates in large part to monitoring the operation of implantable devices as well as memory management of those devices.

In a preferred embodiment the CPU 36 is a microprocessor capable of multitasking monitoring and diagnostic operations. When performing a monitoring or diagnostic routine the microprocessor compares the monitored or sensed data to a range of expected data to determine if a threshold has been exceeded indicating that an event of clinical significance has occurred. The range of expected data may be determined in a variety of ways. One is that the physician may select the range in absolute terms. For example, the physician may program a range of <200 Ω or >3000 Ω to identify a lead impedance problem. A reading of lead impedance that is either too high or too low may act as a threshold event. A threshold event will cause the microprocessor to attempt to save the data that triggered a threshold event and may cause the microprocessor to begin tracking the particular parameter that triggered the threshold event.

Once a threshold event has occurred, i.e. the lead impedance has dropped too low, the microprocessor will first determine whether memory is available to store data regarding lead impedance. If memory is available, the microprocessor will store collected data regarding lead impedance. The microprocessor may also continue to collect lead impedance data to provide further reference data. The historical lead impedance data will then be available to the physician at the next interface with the implantable device.

If no memory is available the microprocessor will determine a priority value for the lead impedance data which triggered the threshold event. The determined priority value can then be compared to equivalent values of the various segments of data already stored in the memory. The priority value (PV) of a segment of data is determined in the preferred embodiment by multiplying the record length (RL) by the assigned clinical significance value (CSV) of the parameter being monitored and inverting that value. The following equation defines the priority value:

$$PV = \frac{1}{RLxCSV}.$$

The clinical significance value is assigned so that the parameter with the highest significance has the lowest number and the lowest significance has the highest number. Correspondingly, the priority value is scaled so that even a parameter that has a high clinical significance, but requires a tremendous use of memory may be determined to be lower priority than a parameter of lower clinical significance that requires substantially less memory. The preferred embodiment disclosed herein is only one way to allocate memory, others will be apparent to those skilled in the art with the benefit of this disclosure. By way of example, the data stored in memory may be date-coded to provide additional support for writing over some portions of memory rather than others. For instance, lead impedance data or other physiologic sensor data may be of high priority when an out-of-bounds condition or threshold violation is first noticed. If, over a period of weeks, however, no other out-of-bounds activity occurs, the stored lead impedance data or other physiologic sensor data may become low priority data.

Another advantage of the present invention is the ability to manage memory through the manipulation of the data stored therein. Referring back to the example just discussed a lead impedance threshold value was violated, but that violation occurred some weeks in the past, rather than continuing to save all the impedance data collected after the threshold condition occurred, the microprocessor may compress the data to the point where only an indication that an out-of-bounds condition occurred on a specific date will be retained. In so doing the microprocessor would be greatly increasing the importance of that data by reducing the record length and therefore, increasing the resulting priority value. In other words, the data was of high clinical significance to start with and now it also takes up very little memory resulting in a very high priority value.

Figure 4A:
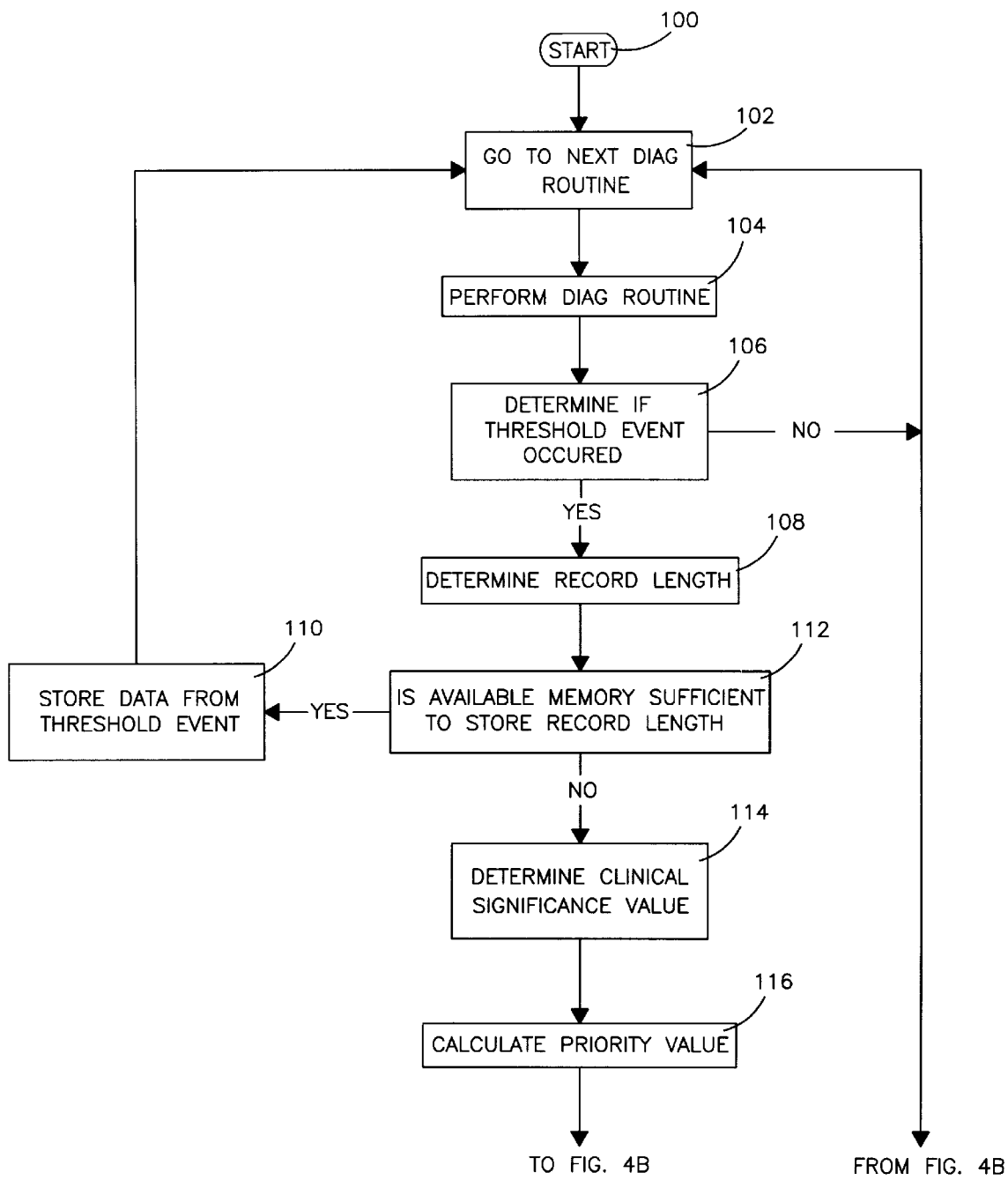
FIG. 4A is a flow diagram of a preferred method of the present invention.
Figure 4B:
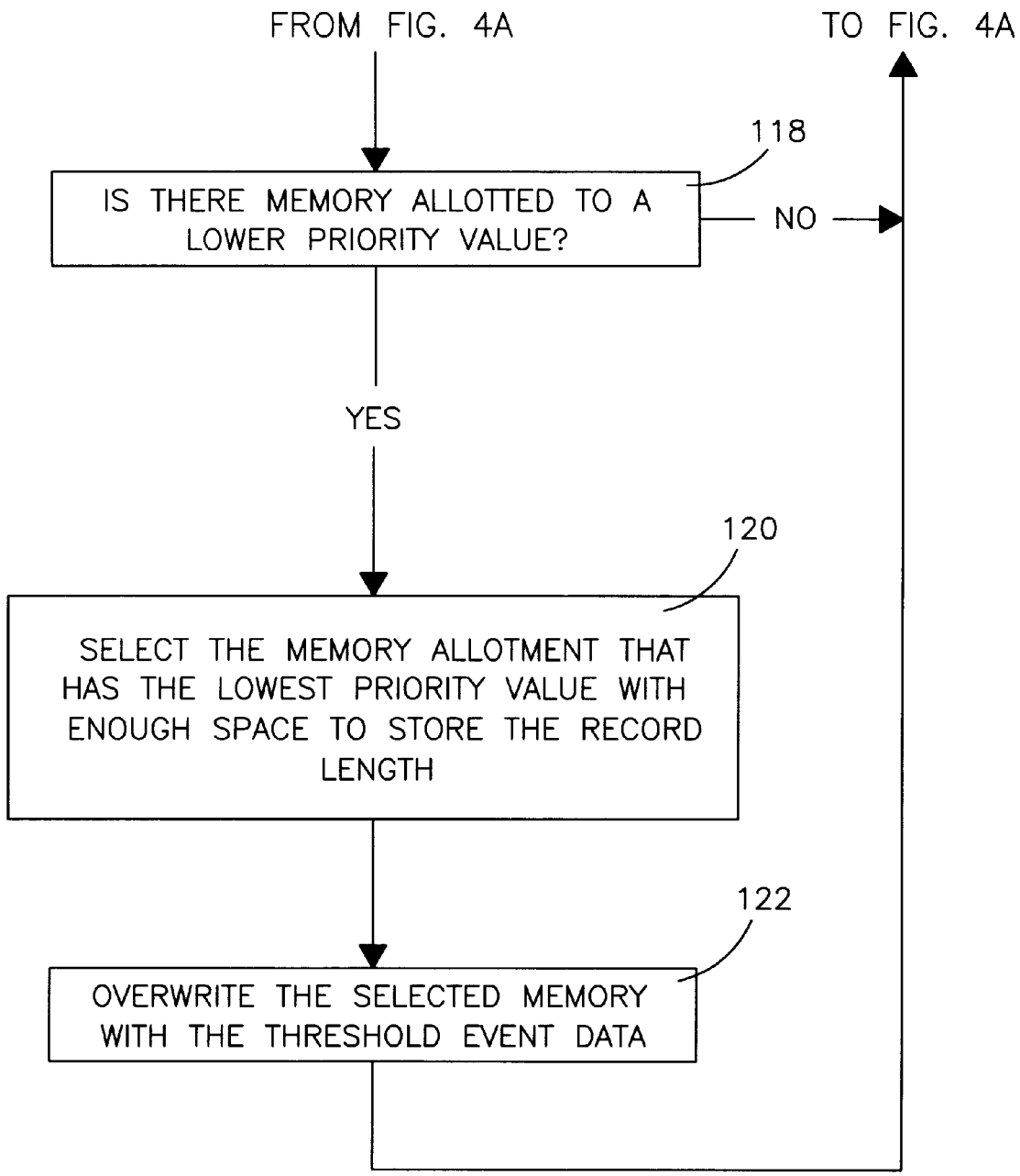
FIG. 4B is a continuation of the flow diagram of FIG. 4A.

The preferred embodiment can be described in greater detail through the use of the flow chart shown in FIGS. 4A and 4B. The microprocessor 36 accesses the next diagnostic or monitoring routine selected to be executed from ROM 34 as shown in box 102. By way of example, the next routine may be to simply monitor the atrial sensor. The microprocessor 36 performs the routine and compares the data that was collected against threshold values stored in memory 34 as shown in box 104. From that comparison the microprocessor 36 determines if a threshold event occurred, 106. If not, the microprocessor selects the next diagnostic routine to be executed and starts the process over again. If a threshold event occurred, the microprocessor 36 determines the record length that will be necessary to store the data related to the threshold event, 108. Once the record length is determined the microprocessor 36 can assess whether the available memory is sufficient to store that record length, 112. If so, the microprocessor 36 stores the data associated with the threshold event in memory 34, as shown in step 110. If not, the microprocessor goes on to determine the clinical significance value of the particular diagnostic threshold event, step 114. Preferably, the microprocessor 36 accesses a clinical significance value stored in memory 34 associated with the particular diagnostic routine selected in step 102. With the record length and the clinical significance value the microprocessor 36 then calculates the priority value, step 116. The clinical significance value determined in step 114 may range from 0 to 10 or any other range selected by the programmer. If the clinical significance is selected so high as to be 0, the record length will have no effect on the calculated priority value. The record length simply identifies the number of bytes that will be required to store the data.

Once the priority value is calculated in step 116, the microprocessor then determines if there is memory allocated to data with a lower associated priority value. If not, the latest threshold event data is not stored because the memory is already filled with data which has higher priority values and therefore higher priority data. At that point the microprocessor will return to step 102 and select the next diagnostic routine to begin again. It will be apparent to one skilled in the art that another level of complexity could be inserted here. For instance, the data that is contained in the allocated memory may be viewed as having two levels of priority. It may be absolutely critical for the physician to know that a ventricular fibrillation (VF) occurred and when. The physician may also desire to examine Electrocardiogram (ECG) data from around the time of the VF event. However, the physician may be willing to forego the ECG data in lieu of receiving data concerning a later occurring lead impedance problem. As such the ECG and other data surrounding the VF threshold event could be compressed to contain only the very essential data to make room for the also significant lead impedance data.

Figure 5:
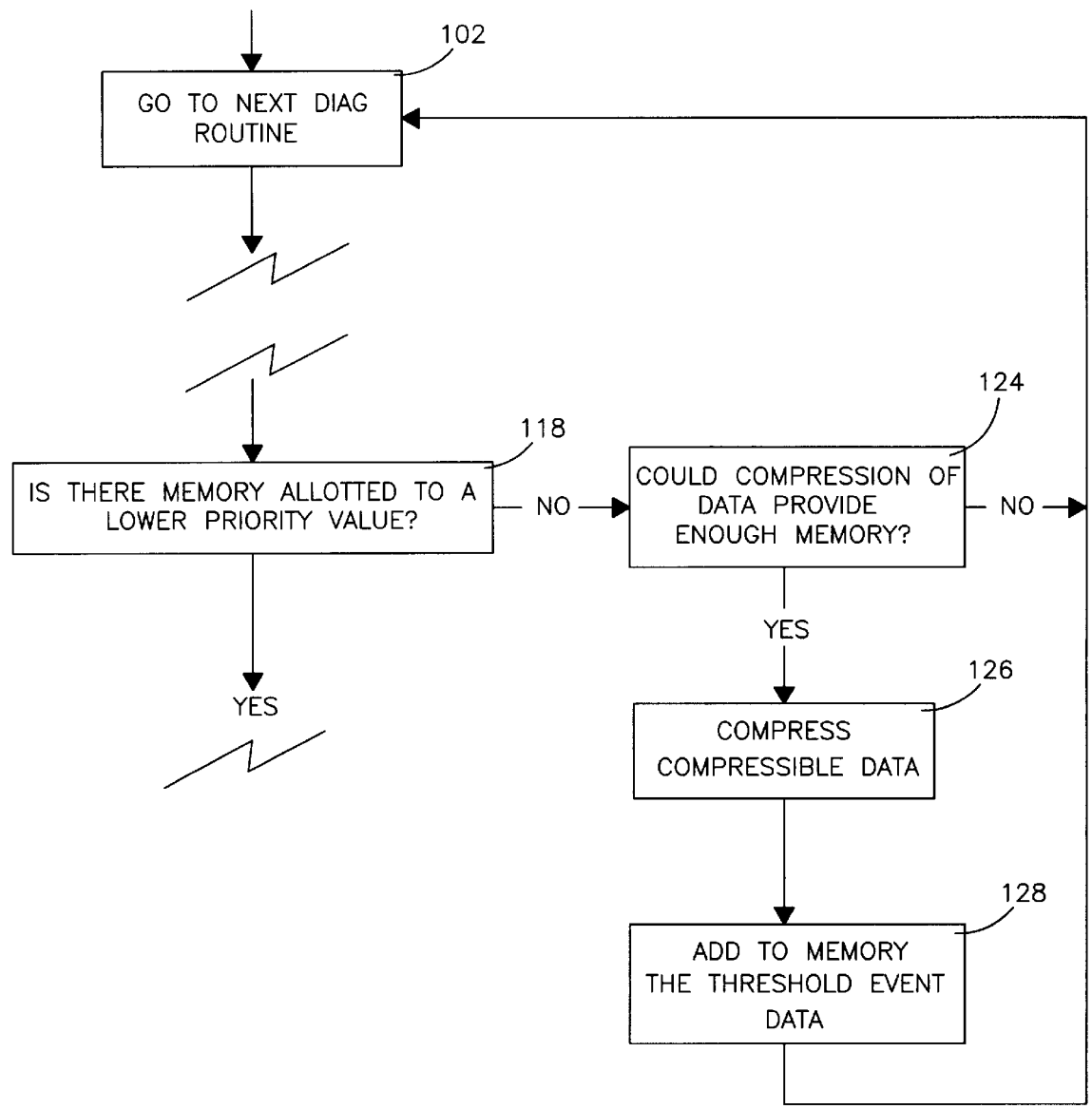
FIG. 5 is a flow diagram of an alternative of the preferred method shown FIGS. 4A and 4B.

The flow chart of FIGS. 4A and 4B could be enhanced as demonstrated in FIG. 5 to account for the two level priority system. If no memory is allocated to a higher priority value from step 118 the microprocessor would then determine if compression of data could provide enough memory to store the new threshold event data, step 124. The compression could be either of the new threshold event data or of any of the data stored in memory. As described in a previous example compression as one extreme could consist of storing only an indication that a particular threshold was breached at a particular date and time. Alternatively, compression may consist of eliminating all but the data collected in the two days following the threshold event, i.e., rather than the last two weeks. As can be seen from these examples, compression is simply a process of overwriting data that the physician might like to see in favor of data the physician needs to have stored.

If compression of data will not provide enough memory space the microprocessor will return to step 102. If the compression will provide the needed space the microprocessor compresses the data which is compressible in step 126. In the step of compressing, the compression need only be performed up to the point where the needed space is then available. After compression, the microprocessor will then add the new threshold event data to the memory in step 128. Once the threshold event data is stored the microprocessor returns to step 102 to execute the next diagnostic routine.

In the preferred embodiment, the diagnostic routines are unchanging and are therefore stored in ROM 34. The parameters which determine whether data collected during the diagnostic routine violates a threshold are generally fixed, but in some limited circumstances may need to be adjusted to customize the system to a particular application. The initial threshold values may be set in a variety of ways. First the threshold values may be specific default values which are contained either in ROM 34 or in the memory of an external programnmer. Upon initialization of the system, the default values stored either internally in ROM 34 or externally in the programmer may be transferred into the RAM 34 for further manipulation and use.

Another alternative for setting threshold values is to allow an implantable device having a physiologic sensor to begin steady state operation and then collect baseline data. The baseline data could then be used to determine threshold events by looking for deviation from baseline by a certain fixed amount or by a certain percentage. A possible hybrid alternative is to use preset default values until enough time has passed to allow true baseline sampling to have occurred. There are any number of equivalent alternatives that one skilled in the art may choose from to select the parameters that will be used by the CPU 36 to determine whether a threshold event has occurred.

The process of setting the clinical significance values for particular threshold events will preferably entail a consideration of the application, a particular patient's medical history, the physician or clinical technician's personal preferences and beliefs, etc. Therefore, while default priority values may be stored internally in ROM 34 or externally in the programmer it is envisioned that once those defaults are copied to the RAM 34, substantial modification may occur.

Determining the record length is performed by the microprocessor 36. The microprocessor 36 assesses the amount of data to be stored immediately as well as the amount of data that will need to be added from future monitoring of the data which originally caused the threshold event.

One application of the present invention is an implantable pacemaker designed to assist a patient suffering from a bradycardia condition. The pacemaker may have some data that is stored continuously, some data that it stores periodically, and some data that gets stored only when a threshold event occurs. One threshold event could be lack of atrial capture. In other words, the pacemaker initiated a paced event in the atrial chamber but sensed no response. The CPU 36 would then follow through with the steps shown in FIG. 1 to eventually store the data. At the next interface the programmer would receive the data concerning loss of atrial capture and would provide an indication to the physician of what the problem may be. For instance, if the data shows that atrial capture has been lost all together the lead may be loose or damaged. If capture is lost only intermittently, the atrial pulse amplitude or atrial pulse width may be set too low for consistent capture.

A further variation on the above example is to provide the capability within the implanted device to make modifications to certain of its own operating parameters to attempt to solve a detected problem. In the example, where intermittent loss of capture occurs, the microprocessor 36 may be programmed to not only identify that data related to loss of capture should be stored, but may also be programmed to identify the potential problem and begin to take remedial action. The microprocessor 36 could begin increasing the atrial pulse amplitude or width to either achieve capture 100% of the time, or in the alternative determine that the problem is not with the atrial pulse amplitude or width settings but instead may be an intermittently faulty lead. The microprocessor 36 would then store not only data associated with the threshold event, but would store data concerning attempted remedial action for access by the programmer at the next interface.

The specific examples set out herein are not intended to limit the present invention in any way, but rather are intended to assist in a complete understanding of the present invention as it is set out in the claims below.

What is claimed is:

1. A method executable by a body-implantable device having at least one physiologic sensor, comprising the steps of:

receiving sensor data from the physiologic sensor;

determining whether said sensor data exceeds a threshold value;

determining for said sensor data which exceeds said threshold value, whether sufficient memory is available to store said sensor data;

determining a priority value for said sensor data;

determining if data with a lower priority value exists in memory, and overwriting with said sensor data said data with a lower priority value;

wherein said step of determining said priority value involves taking into account the amount of memory required to store said sensor data and a clinical significance value associated with said sensor data.

2. The method of claim 1, wherein said body-implantable device is a pacemaker.

3. A method of allocating a limited amount of memory in a body implantable device having at least one implantable physiologic sensor, comprising the steps of:

determining the clinical significance of data received from the at least one physiological sensor;

storing data received from the at least one physiologic sensor that is of clinical significance in a memory as it is received until new data is received from the sensor that is of clinical significance for which there is not enough space in memory for said new data to be stored;

determining whether compression of the data in said memory would create enough memory space for said new data;

compressing the data; and storing said new data in said memory.

4. The method of claim 3 wherein said body implantable device is a pacemaker.

* * * * *